(12) United States Patent
Schwartz et al.

(10) Patent No.: US 6,997,924 B2
(45) Date of Patent: Feb. 14, 2006

(54) LASER PULMONARY VEIN ISOLATION

(75) Inventors: Yitzhack Schwartz, Haifa (IL); Assaf Govari, Haifa (IL); Shlomo Ben-Haim, Haifa (IL); Uri Yaron, Zichron-Yaccov (IL); Marcia Leatham, Orange, CA (US)

(73) Assignee: Biosense Inc., New Brunswick, NJ (US)

( * ) Notice: Subject to any disclaimer, the term of this patent is extended or adjusted under 35 U.S.C. 154(b) by 249 days.

(21) Appl. No.: 10/245,613

(22) Filed: Sep. 17, 2002

(65) Prior Publication Data

US 2004/0054360 A1 Mar. 18, 2004

(51) Int. Cl.
*A61B 18/18* (2006.01)

(52) U.S. Cl. .............................. 606/15; 606/7; 606/17; 606/18; 607/7; 607/88; 607/89; 128/898

(58) Field of Classification Search ............... 606/3, 606/7, 10, 13–18; 607/5, 7, 88, 89; 128/898
See application file for complete search history.

(56) References Cited

U.S. PATENT DOCUMENTS

| 4,979,948 A | 12/1990 | Geddes et al. |
| 5,109,859 A | 5/1992 | Jenkins |
| 5,242,438 A | 9/1993 | Loeb |
| 5,366,490 A | 11/1994 | Edwards et al. |

(Continued)

FOREIGN PATENT DOCUMENTS

| WO | WO 00/67656 A2 | 11/2000 |
| WO | WO 01/72373 A2 | 10/2001 |
| WO | WO 01/82778 A2 | 11/2001 |

OTHER PUBLICATIONS

European Search Report EP 03255782 dated Dec. 4, 2003.

Pappone C, Rosanio S, Oreto G, Tocchi M, Gugliotta F, Vicedomini G, Salvati A, Dicandia C, Mazzone P, Santinelli V, Gulletta S, Chierchia S, *Circumferential Radiofrequency Ablation of Pulmonary Vein Ostia: A New Anatomic Approach for Curing Atrial Fibrillation*, Circulation 102:2619–2628 (2000).

Natale A, Pisano E, Shewchik J, Bash D, Fanelli R, MD; Potenza D; Santarelli P; Schweikert R; White R; Saliba W; Kanagaratnam L; Tchou P; Lesh M, *First Human Experience With Pulmonary Vein Isolation Using a Through-the-Balloon Circumferential Ultrasound Ablation System for Recurrent Atrial Fibrillation*, Circulation 102:1879–1882 (2000).

Scheinman MM, Morady F. Nonpharmacological Approaches to Atrial Fibrillation. *Circulation* 2001;103:2120–2125.

Wang PJ, Homoud MK, Link MS, Estes III NA, Alternate energy sources for catheter ablation. *Curr Cardiol Rep* 1999 Jul;1(2):165–171.

(Continued)

*Primary Examiner*—A. Farah
(74) *Attorney, Agent, or Firm*—Louis L. Capezzuto (57) ABSTRACT

A catheter introduction apparatus provides an optical assembly for emission of laser light energy. In one application, the catheter and the optical assembly are introduced percutaneously, and transseptally advanced to the ostium of a pulmonary vein. An anchoring balloon is expanded to position a mirror near the ostium of the pulmonary vein, such that light energy is reflected and directed circumferentially around the ostium of the pulmonary vein when a laser light source is energized. A circumferential ablation lesion is thereby produced, which effectively blocks electrical propagation between the pulmonary vein and the left atrium.

23 Claims, 5 Drawing Sheets

U.S. PATENT DOCUMENTS

| | | | |
|---|---|---|---|
| 5,433,708 A | | 7/1995 | Nichols et al. |
| 5,693,043 A | * | 12/1997 | Kittrell et al. ............... 606/15 |
| 5,840,025 A | | 11/1998 | Ben-Haim |
| 5,891,134 A | | 4/1999 | Coble et al. |
| 5,938,600 A | | 8/1999 | Van Vaals et al. |
| 5,971,983 A | | 10/1999 | Lesh |
| 6,004,269 A | | 12/1999 | Crowley et al. |
| 6,012,457 A | | 1/2000 | Lesh |
| 6,024,740 A | | 2/2000 | Lesh et al. |
| 6,053,909 A | * | 4/2000 | Shadduck ...................... 606/3 |
| 6,064,902 A | | 5/2000 | Haissaguerre et al. |
| 6,090,084 A | | 7/2000 | Hassett et al. |
| 6,117,101 A | | 9/2000 | Diederich et al. |
| 6,164,283 A | * | 12/2000 | Lesh .......................... 128/898 |
| 6,190,382 B1 | | 2/2001 | Ormsby et al. |
| 6,245,064 B1 | | 6/2001 | Lesh et al. |
| 6,251,109 B1 | | 6/2001 | Hassett et al. |
| 6,679,269 B1 | * | 1/2004 | Swanson .................... 128/898 |
| 2001/0041880 A1 | | 11/2001 | Brisken et al. |
| 2002/0065512 A1 | | 5/2002 | Acker |
| 2003/0125726 A1 | | 7/2003 | Maguire et al. |

OTHER PUBLICATIONS

Fried NM, Lardo AC, Berger RD, Calkins H, Halperin HR, Linear lesions in myocardium created by Nd:YAG laser using diffusing optical fibers: in vitro and in vivo results, *Laser Surg Med 2000*;27(4) :295–304.

Keane D, Ruskin J, Linear atrial ablation with a diode laser and fiber optic catheter. *Circulation* 1999; 100:e59–e60.

Ware D, et al., Slow intramural heating with diffused laser light: A unique method for deep myocardial coagulation. *Circulation*; Mar. 30, 1999; pp. 1630–1636.

European Search Report EP04250864 dated May 27, 2004.

Christian Dorme et al. Ultrasonic Beam Steering Through Inhomogeneous Layers With A Time Reversal Mirror. IEEE Transactions on Ultrasonics, Ferroelectrics, and Frequency Control, vol. 43, No. 1, Jan. 1996.

M. Fink et al. Self Focusing In Inhomogeneous Media With "Time Reversal" Acoustic Mirrors. 1989 Ultrasonics Symposium —681,.

Mathias Fink Time Reversal Of Ultrasonic Fields —Part 1: Basic Principles. IEEE Transactions on Ultrasonics, Ferroelectrics, and Frequency Control, vol. 39, No. 5, Sep. 1992.

Mickaël Tanter et al. Focusing and Steering Through Absorbing and Aberrating Layers: Application to Ultrasonic Propagation Through the Skull. J. Acoust. Soc. Am 103(5) Pt. 1, May 1998.

MickaëTanter et al. Focusing Through Skull with Time Reversal Mirrors. Application to Hyperthermia. 1996 IEEE Ultrasonics Symposium—1289.

Francois Wu et al. Time Reversal of Ultrasonic Fields—Part II: Experimental Results. IEEE Transactions on Ultrasonics, Ferroelectrics, and Frequency Control, vol. 39, No. 5, Sep. 1992.

Eigier NL et al., "Implantation and Recovery of Temporary Metallic Stents in Canine Coronary Arteries", J Am Coll Cardiol 1993:22(4)1207–1213.

Middleton JC et al., "Synthetic Biodegradable Polymers Orthopedic Devices", Biomaterials 21 (2000) 2335–2346.

European Search Report EP03257414 dated Apr. 5, 2004.

* cited by examiner

LASER PULMONARY VEIN ISOLATION

BACKGROUND OF THE INVENTION

1. Field of the Invention

This invention relates to methods and apparatus for the medical treatment of disease of the heart. More particularly, this invention relates to a method and apparatus for treating cardiac arrhythmias by ablating in a vicinity of pulmonary venous tissue.

2. Description of the Related Art

Tissue ablation from the inner walls of hollow viscera of the body generally, and the vascular system in particular, has been found to be useful in the treatment of various medical conditions. Technological developments in intravascular catheters, manipulative instruments adapted to intravascular catheters, and catheter localization techniques have especially benefited the field of cardiology. Percutaneous transcatheter ablation has been used successfully in the treatment of conduction defects and arrhythmias of various types. Today, atrial tachyarrhythmias are a common application for ablative therapy.

Various ablative modalities have been employed in the past, such as ablation by direct heating. Energy can be conducted to the target tissue using various modalities, such as ultrasound, laser, resistive heating, and radiofrequency energy.

One ablative approach is the so-called "maze" technique. In general, the maze procedure attempts to block abnormal conduction patterns in the left atrium by establishing a maze-like pattern of linear lesions in the left atrial wall.

Atrial arrhythmias are known to be associated with abnormal electrical activity of tissue foci in the vicinity of the pulmonary veins, especially the superior pulmonary veins. Various ablative treatments of such foci have been attempted. For example, the production of linear atrial lesions by radiofrequency ablation, in combination with ablation of suspected arrhythmogenic foci has been performed using transcatheter techniques.

More recently, circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

U.S. Pat. No. 5,468,239 to Tanner et al. describes a circumferential laser assembly, adapted, for example, to be placed in the urethral canal such that a transurethral resection of benign prostatic hypertrophy may be performed.

Radiofrequency ablation using multiple contiguous circumferential points, guided by electro-anatomical mapping is proposed in the document, *Circumferential Radiofrequency Ablation of Pulmonary Vein Ostia: A New Anatomic Approach for Curing Atrial Fibrillation*, Pappone C, Rosanio S, Oreto G, Tocchi M, Gugliotta F, Vicedomini G, Salvati A, Dicandia C, Mazzone P, Santinelli V, Gulletta S, Chierchia S, Circulation 102:2619–2628 (2000). It is emphasized that particular care must be exercised to ensure that the ablation sites are indeed contiguous; otherwise irregular electrical activity in the pulmonary vein may continue to contribute to atrial arrhythmia.

It has also been proposed to produce circumferential ablative lesions using ultrasound energy delivered via a cylindrical ultrasound transducer through a saline-filled balloon. This technique is described in the document, *First Human Experience With Pulmonary Vein Isolation Using a Through-the-Balloon Circumferential Ultrasound Ablation System for Recurrent Atrial Fibrillation*, Natale A, Pisano E, Shewhik J, Bash D, Fanelli R, MD; Potenza D; Santarelli P; Schweikert R; White R; Saliba W; Kanagaratnam L; Tchou P; Lesh M, Circulation 102:1879–1882 (2000). Ablation times in the order of 2 minutes are reported.

A known drawback in the use of ultrasound energy for cardiac tissue ablation is the difficulty in controlling the local heating of tissue. There are tradeoffs between the clinical desire to create a sufficiently large lesion to effectively ablate an abnormal tissue focus, or block an aberrant conduction pattern, and the undesirable effects of excessive local heating. If the ultrasound device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

In consideration of these, and other factors, it is appropriate, in designing a practical energy emitter, to consider the amplitude of the energy signal, the amount of time required for the energy application, the size of the emitter, and the contact area, as well as ease of positioning, withdrawal, and repositioning of the device so as to be able to conveniently produce multiple lesions during the same medical procedure.

Previous approaches to controlling local heating include the inclusion of thermocouples within the electrode and feedback control, signal modulation, local cooling of the catheter tip, and fluid assisted techniques, for example perfusion of the target tissue during the energy application, using chilled fluids. Typical of the last approach is Mulier, et al. U.S. Pat. No. 5,807,395.

Publications which describe various medical techniques of interest include:

Scheinman M M, Morady F. Nonpharmacological Approaches to Atrial Fibrillation. *Circulation* 2001; 103:2120–2125.

Wang P J, Homoud M K, Link M S, Estes III N A. Alternate energy sources for catheter ablation. *Curr Cardiol Rep* 1999 Jul;1(2):165–171.

Fried N M, Lardo A C, Berger R D, Calkins H, Halperin H R. Linear lesions in myocardium created by Nd:YAG laser using diffusing optical fibers: in vitro and in vivo results. *Lasers Surg Med* 2000;27(4):295–304.

Keane D, Ruskin J, Linear atrial ablation with a diode laser and fiber optic catheter. *Circulation* 1999; 100:e59-e60.

Ware D, et al., Slow intramural heating with diffused laser light: A unique method for deep myocardial coagulation. *Circulation*; Mar. 30, 1999; pp. 1630–1636.

Other medical technologies of interest are described in U.S. Pat. No. 5,891,134 to Goble et al., U.S. Pat. No. 5,433,708 to Nichols et al., U.S. Pat. No. 4,979,948 to Geddes et al., U.S. Pat. No. 6,004,269 to Crowley et al., U.S. Pat. No. 5,366,490 to Edwards et al., U.S. Pat. Nos. 5,971,983, 6,164,283, and 6,245,064 to Lesh, U.S. Pat. No. 6,190,382 to Ormsby et al., U.S. Pat. Nos. 6,251,109 and 6,090,084 to Hassett et al., U.S. Pat. No. 5,938,60 to Swartz et al., U.S. Pat. No. 6,064,902 to Haissaguerre et al., and U.S. Pat. No. 6,117,101 to Diederich et al.

All of the patents and publications cited in this disclosure are incorporated herein by reference.

SUMMARY OF THE INVENTION

It is therefore a primary object of some aspects of the present invention to provide improved apparatus and method for electrically isolating the pulmonary vein by accomplishing a circumferential conduction block surrounding the pulmonary vein ostium in a single ablation application of laser light energy.

It is another object of some aspects of the present invention to reduce the time required to perform isolation of the pulmonary veins using a laser.

A catheter introduction apparatus provides an optical assembly for emission of laser light energy. In one application, the catheter and the optical assembly are introduced percutaneously, and transseptally advanced to the ostium of a pulmonary vein. An anchor such as an anchoring balloon is expanded to center a mirror in front of the ostium of the pulmonary vein, such that light energy is reflected from the mirror circumferentially onto the wall of the pulmonary vein when a laser light source is energized. A circumferential ablation lesion is produced around the ostium of the pulmonary vein, which effectively blocks electrical propagation between the pulmonary vein and the left atrium.

The invention provides a method for electrically isolating a cardiac chamber, including the steps of introducing an optical assembly at a pulmonary vein proximate its ostium, anchoring the optical assembly at the pulmonary vein, and thereafter conducting laser light energy in a path extending from the optical assembly to a circumferential ablation region of the pulmonary vein.

According to an aspect of the method, the path avoids the anchor.

According to another aspect of the method, conducting the laser light energy is performed by directing the laser light energy into a circumferential line that intersects the ablation region.

In another aspect of the method, the anchor is a balloon, and anchoring is performed by expanding the balloon to engage the pulmonary vein.

In a further aspect of the method, the optical assembly is introduced via the fossa ovalis, and preliminary laser light energy is directed onto the fossa ovalis to ablate tissue thereof to facilitate passage of the optical assembly therethrough.

In yet another aspect of the method, conducting the laser light energy is performed in exactly one application.

In still another aspect of the method, conducting the laser light energy is performed in a series of pulses.

According to another aspect of the method, the duration of each of the pulses is less than 100 milliseconds.

In an additional aspect of the method, introducing the optical assembly is performed by disposing the optical assembly on an intravascular catheter, and passing the distal portion of the intravascular catheter through a blood vessel into the heart.

In one aspect of the method, conducting the laser light energy also includes reflecting the laser light energy.

According to a further aspect of the method, reflecting the laser light energy includes disposing a mirror in a path of the laser light energy external to the anchor.

According to yet another aspect of the method, reflecting the laser light energy includes disposing a light-reflective coating on an external surface of the anchor and reflecting the laser light energy from the light-reflective coating.

According to still another aspect of the method, the laser light energy has a wavelength of about 13,000 nm.

The invention provides an apparatus for electrically isolating a cardiac chamber, including an intravascular catheter adapted for introduction into a pulmonary vein proximate an ostium thereof, an anchor disposed at a distal end of the catheter for fixation of the catheter tip at the pulmonary vein, and an optical assembly for conducting laser light energy in a path extending to a circumferential ablation region of the pulmonary vein.

According to an aspect of the apparatus, the optical assembly is in a non-contacting relationship with the anchor.

According to yet another aspect of the apparatus, the path avoids the anchor.

According to an additional aspect of the apparatus, the optical assembly includes an optical fiber for conducting the laser light energy from a light source, a lens disposed at an exit face of the optical fiber, and a reflector disposed in the path external to the anchor for directing the laser light energy into a circumferential line that intersects the ablation region.

According to an additional aspect of the apparatus, the lens is a graded index lens.

According to one aspect of the apparatus, the reflector is a parabolic mirror.

According to another aspect of the apparatus, the reflector is a light reflecting external surface of the anchor.

According to one aspect of the apparatus, the anchor includes a balloon that inflates to engage the pulmonary vein.

According to an additional aspect of the apparatus, the balloon is bilobate.

According to one aspect of the apparatus, a proximal portion of the balloon is more expanded than a distal portion of the balloon in an inflated state thereof.

According to another aspect of the apparatus, the laser light energy is applied to the ablation region in exactly one application.

According to a further aspect of the apparatus, the laser light energy is applied to the ablation region in a series of pulses.

According to yet another aspect of the apparatus, the duration of each of the pulses is less than 100 milliseconds.

According to still another aspect of the apparatus, the laser light energy has a wavelength of about 1.3 microns.

BRIEF DESCRIPTION OF THE DRAWINGS

For a better understanding of these and other objects of the present invention, reference is made to the detailed description of the invention, by way of example, which is to be read in conjunction with the following drawings, wherein:

FIG. 1 illustrates a therapeutic catheter that is constructed and operative in accordance with a preferred embodiment of the invention and FIG. 1B illustrates an enlarged view of a distal end of the catheter of FIG. 1A;

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well known circuits, control logic, and other apparatus have not been shown in detail in order not to unnecessarily obscure the present invention.

Figures 1A, 1B:
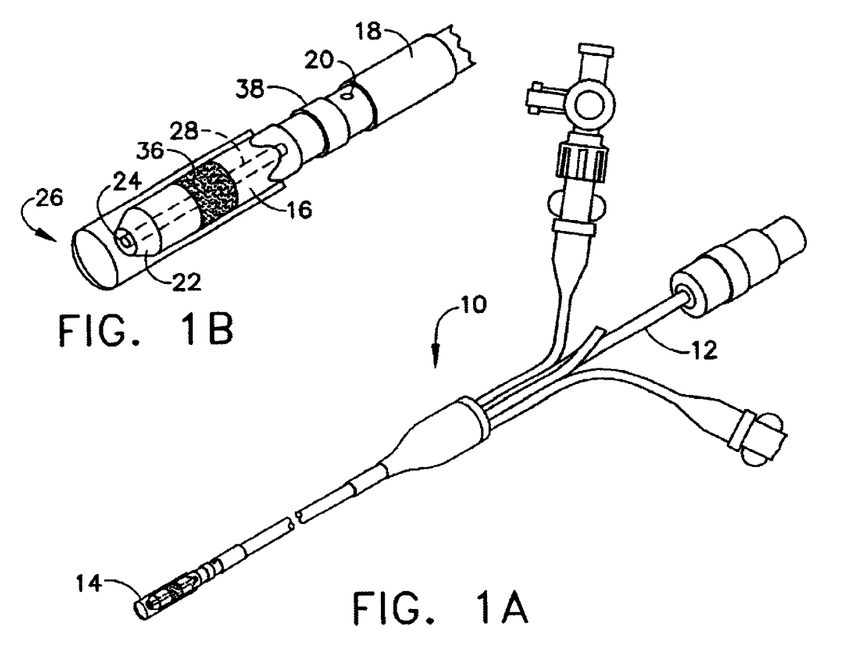

Turning now to the drawings, reference is made to FIG. 1A and 1B, which illustrate a medical device that is constructed and operative in accordance with a preferred embodiment of the invention. An intravascular catheter 10 has a proximal end 12 and a distal end 14. The distal end 14 is provided with at least one seal 16, and optionally a second seal 18. The seals 16, 18 are preferably inflatable balloons, made from rubber, polyurethane, or a similar elastic material. The catheter 10 has one or more lumens, which conduct fluid for inflating and deflating the seals 16, 18. One of the lumens terminates in a port 20, and is useful for injection of fluids and withdrawal of blood as may be required during use. Other lumens are provided for passage of guidewires and instruments therethrough. An inflatable anchoring balloon 22, shown in a deflated condition, is located distal to the seals 16, 18. The catheter 10 also has a coaxial guidewire lumen 24.

Figure 2:
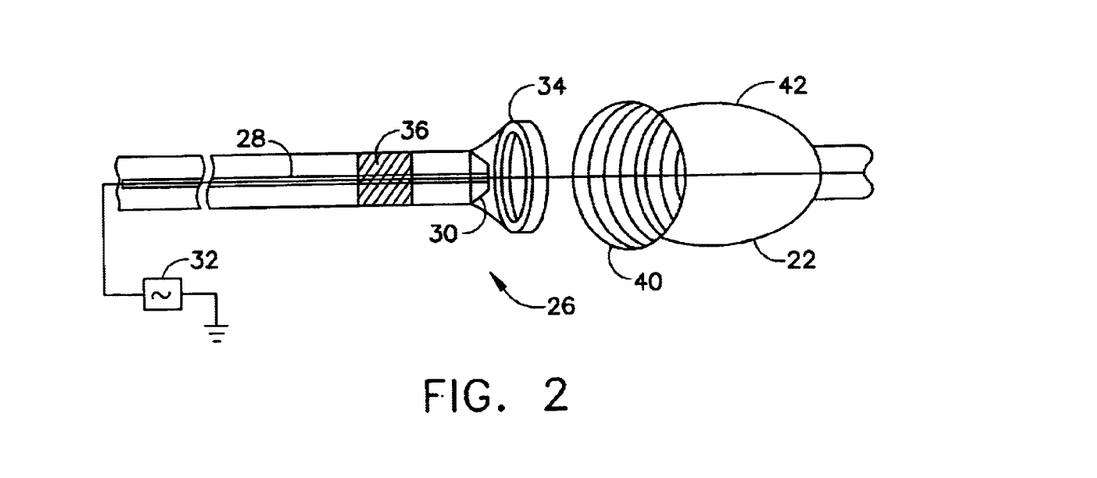
FIG. 2 is an enlarged schematic illustration of the distal end of the catheter shown in FIG. 1 with an inflation balloon expanded, and an optical fiber and associated optics in place, in accordance with respective preferred embodiments of the present invention.

Reference is now made to FIG. 2, which is a schematic enlarged view of the distal end 14 of a catheter that is constructed and operative in accordance with a preferred embodiment of the invention, similar to the catheter 10 (FIG. 1A), in which like elements are given like reference numerals. Disposed near the distal end 14 of the catheter 10 (FIG. 10) is a laser subassembly 26, which includes an optical fiber 28, shown in a position proximate the lumen 24, which conveys laser light through a lens 30 to a mirror (FIG. 3) or a light-reflective coating (FIG. 4), which in turn reflects the laser light circumferentially onto a target. The laser subassembly 26 is preferably disposed external to and in a non-contacting relationship with the anchoring balloon 22. Thus in many embodiments, the anchoring balloon 22 need not directly support the laser subassembly 26, and is excluded from the laser light path. An advantage of this arrangement is that standard catheter balloons can be used in the catheter 10.

Introduced slidably via the lumen 24, the optical fiber 28 extends to and is connected proximally to a suitable external laser light source 32. For some applications, a mirror 34 is rigidly fixed in position with respect to the catheter body or a structural component thereof. It will be appreciated that whereas the mirror 34 is shown by way of illustration, other optical elements known in the art (e.g., lenses) may also be configured for use with some embodiments of the invention.

In a preferred embodiment, the active sites to be ablated are identified using the location and mapping system disclosed in commonly assigned U.S. Pat. No. 5,840,025, which is herein incorporated by reference. Certain components of the location and mapping system are incorporated into the distal end 14 of the catheter 10, namely a sensor 36 and a transmitting antenna 38 (FIGS. 1A and 1B), which can be a dipole antenna. The sensor 36 detects local electrical activity of the heart, and the antenna 38 transmits signals to a plurality of receiving antennae (not shown) which are placed on the body surface of a patient during use. The distal end 14 can be radio-opaque, in order to facilitate its localization by conventional radiographic techniques, alternatively or in addition to the system disclosed in the above-noted U.S. Pat. No. 5,840,025.

In embodiments in which the system disclosed in the above-noted U.S. Pat. No. 5,840,025 is not used, the sensor 36 performs conventional monitoring of local electrical activity, and the antenna 38 can be omitted.

The anchoring balloon 22 is inflated, and preferably has a large-radius proximal lobe or segment 40, and a small-radius distal lobe or segment 42. Typically the anchoring balloon 22 measures 1 cm in length and has a caliber of about 2.7 mm. (8 French) when uninflated, expanding to 3–4 cm when inflated. The bilobate configuration of the anchoring balloon 22 aids in securely positioning the anchoring balloon 22 within the ostium of a pulmonary vein. Alternatively the anchoring balloon 22 can be pyriform, ellipsoidal, or otherwise constructed, preferably such that its proximal portion is more radially expanded than its distal portion. The anchoring balloon 22 is constructed of conventional materials. Proximally, a connection between the optical fiber 28 and the laser light source 32 is illustrated.

In some embodiments, the anchoring balloon 22 is coated with a light-reflective coating (FIG. 4), and is positioned so as to reflect the light from the laser subassembly 26 to the endocardial wall and thereby facilitate the circumferential ablation around the pulmonary vein. In these embodiments, the mirror 34 is typically omitted, and a light-reflective coating directs the laser light circumferentially and directly towards the ablation zone.

Figure 3:
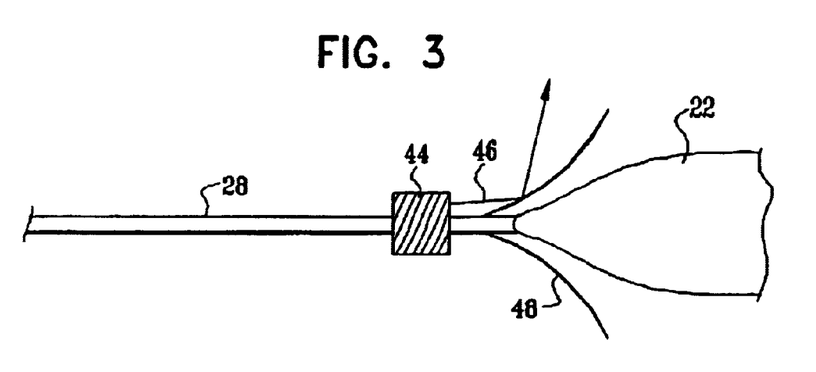
FIG. 3 is a schematic sectional view of a laser subassembly employing a parabolic mirror, taken along the axis of a catheter in accordance with a preferred embodiment of the invention.

Reference is now made to FIG. 3, which is a schematic sectional view of the laser subassembly 26 (FIG. 2) taken along the axis of the optical fiber 28 in accordance with a preferred embodiment of the invention. The description of FIG. 3 should be read in conjunction with FIG. 2, in which like elements are given like reference numerals. The optical fiber 28 is coupled at its exit face to a graded index (GRIN) rod lens 44, which serves as a relay lens for light passing through the optical fiber 28. As shown by an exemplary ray 46, light exiting the lens 44 strikes a mirror 48 that is disposed between the lens 44 and the anchoring balloon 22, and is then reflected. The mirror 48 is a 360 degree parabolic mirror, which is symmetric about the axis of the catheter 10 (FIG. 1A), so that when the apparatus is positioned, the reflected light strikes the ablation zone as a circumferential beam.

Figure 4:
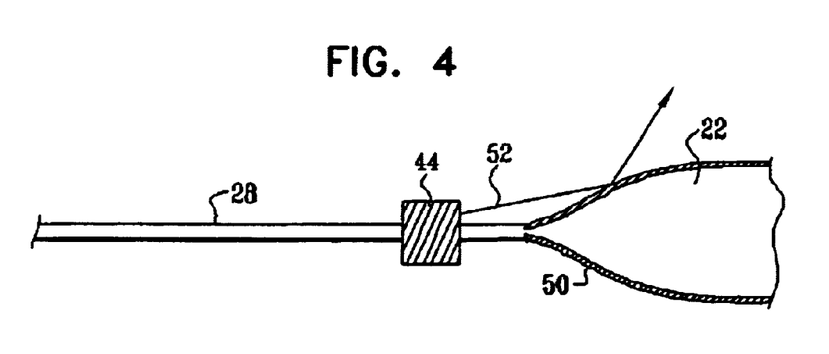
FIG. 4 is a schematic sectional view of a laser subassembly employing a light-reflective coating taken along the axis of a catheter in accordance with an alternate embodiment of the invention.

Reference is now made to FIG. 4, which is a schematic sectional view of a laser subassembly taken along the axis of the optical fiber 28 in accordance with an alternate embodiment of the invention. The description of FIG. 4 should be read in conjunction with FIG. 2 and FIG. 3, in which like elements are given like reference numerals. The arrangement shown in FIG. 4 is similar to that of FIG. 3, except that the mirror is omitted. Instead a light-reflective coating 50 is disposed on the external surface of the anchoring balloon 22. As shown by an exemplary ray 52, light exiting the lens 44 strikes the light-reflective coating 50, and is then reflected. When the apparatus is positioned, the reflected light strikes the ablation zone as a circumferential beam.

Figure 5:
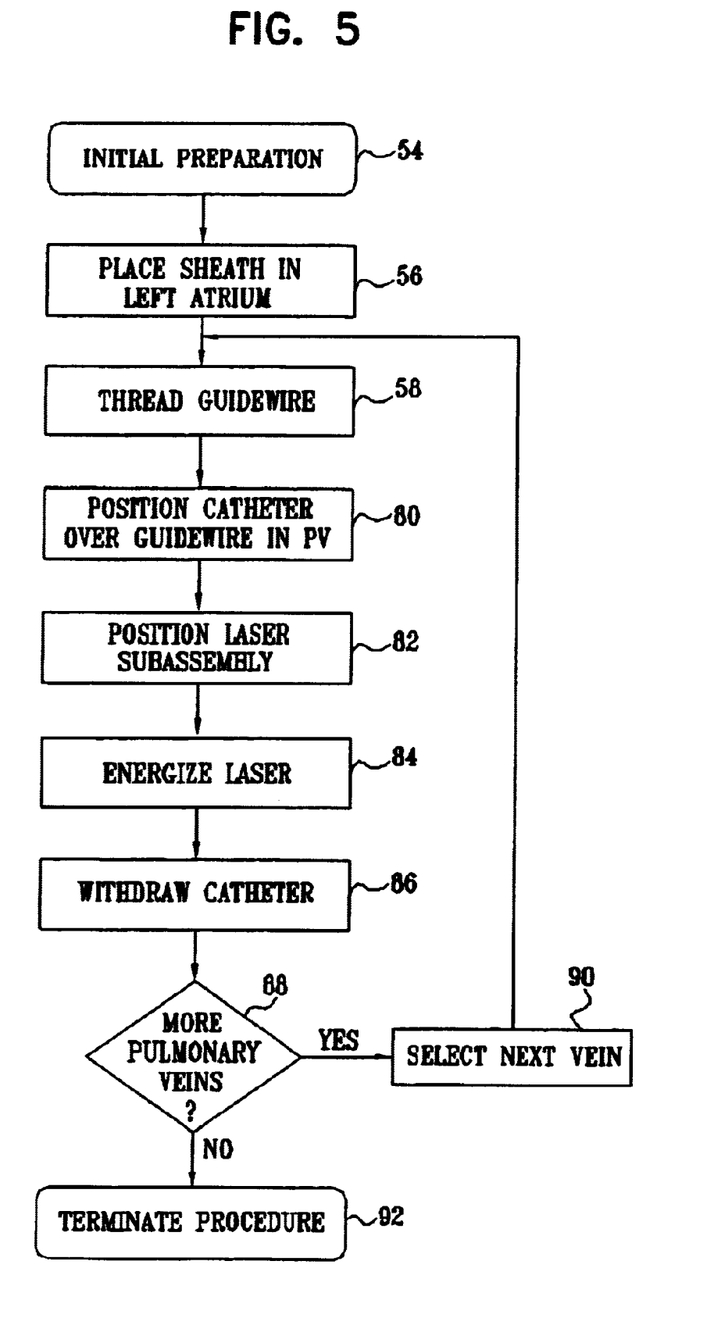
FIG. 5 is a flow chart of a method for electrically isolating pulmonary veins, which is operative in accordance with a preferred embodiment of the invention.

Reference is now made to FIG. 5, which is a flow chart of a method for electrically isolating pulmonary veins, which is operative in accordance with a preferred embodiment of the invention. The description of FIG. 5 should be read in conjunction with FIGS. 1A and 1B, FIG. 3, and FIG. 4.

In initial step 54 routine preparation of a subject (not shown) and equipment are accomplished. This includes attachment of various monitoring and grounding leads, as may be required for electrophysiological monitoring of the procedure and for the operation of the above-noted location and mapping system.

Next, at step 56, a series of events begins, ultimately leading to the positioning of the catheter 10 and the laser subassembly 26 at the ostium of a pulmonary vein. Step 56 is typically conventional. In a preferred approach, the venous system is accessed using the well-known Seldinger technique, in which an introducer sheath is positioned in a peripheral vein, typically a femoral vein. A guiding sheath is introduced through the introducer sheath, and is advanced via the inferior vena cava into the right atrium. Then, using a Brockenbrough needle, the fossa ovalis of the interatrial septum is punctured, and the puncture dilated if necessary. The Brockenbrough needle is withdrawn, and the guiding sheath placed in the left atrium. Alternatively, the ablation catheter is energized as it contacts the interatrial septum, usually at the fossa ovalis, in order to ablate a portion of the fossa ovalis. Ablation of septal tissue eases the passage of the catheter through the septum, reduces the amount of hardware used, and shortens the procedure, as it is not necessary to pass a dilator through the fossa ovalis. Ablation of septal tissue typically requires a power output of less than 70 watts. It is also possible to access the left atrium via the superior vena cava, or to use a retrograde intra-arterial technique.

Next, in step 58 a guidewire is advanced through the guiding sheath, through the left atrial chamber, into a pulmonary vein.

The order in which the specific pulmonary veins are visited and treated is arbitrary, but it is preferable to concentrate first on the two superior pulmonary veins, in which the muscular sleeves are more prominent than in the inferior pulmonary veins. Thereafter the inferior pulmonary veins may be isolated. Typically, an ablation procedure involves the isolation of all four pulmonary veins.

Figure 6:
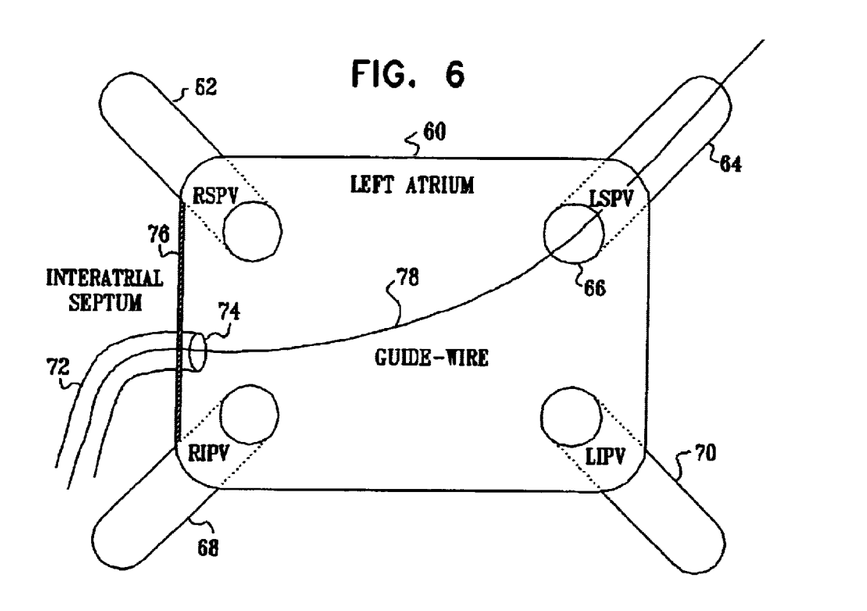
FIG. 6 schematically illustrates certain aspects of a method of intracardiac catheter access during a first phase of the method shown in FIG. 5.

Reference is now made to FIG. 6, which schematically illustrates certain aspects of the method of electrical pulmonary vein isolation in accordance with a preferred embodiment of the invention. The description of FIG. 6 should be read in conjunction with FIG. 5. FIG. 6 represents the status at the completion of step 58 (FIG. 5). A cutaway view of a left atrial chamber 60 includes a right superior pulmonary vein 62 and a left superior pulmonary vein 64, whose ostium 66 is indicated. The view of FIG. 6 also includes a right inferior pulmonary vein 68, and a left inferior pulmonary vein 70. A conventional guiding sheath 72 has a distal end 74 which has been positioned on the left atrial side of an interatrial septum 76. A conventional guidewire 78 extends through the lumen of the guiding sheath 72, into the lumen of the left superior pulmonary vein 64. It will be understood that while the guidewire 78 is shown in relation to the left superior pulmonary vein 64, the technique is equally applicable to the other pulmonary veins.

Referring again to FIG. 5, at step 80 the guiding sheath is withdrawn, and an ablation catheter is slidably tracked over the guidewire, using the guidewire lumen of the catheter. The catheter is advanced into the left atrium. While maneuvering the catheter in the heart, its position is preferably monitored by the location and mapping system disclosed in the above-noted U.S. Pat. No. 5,840,025, or alternatively by conventional imaging modalities. The anchoring balloon of the catheter is deflated during the positioning maneuver. The tip of the catheter is advanced until it is located at the ostium of a pulmonary vein, such that a first segment of the catheter's anchoring balloon, which is substantially the balloon's proximal third, is disposed in the left atrium, and a second segment of the anchoring balloon, composed of its remaining distal portion, lies within the lumen of the pulmonary vein.

Figure 7:
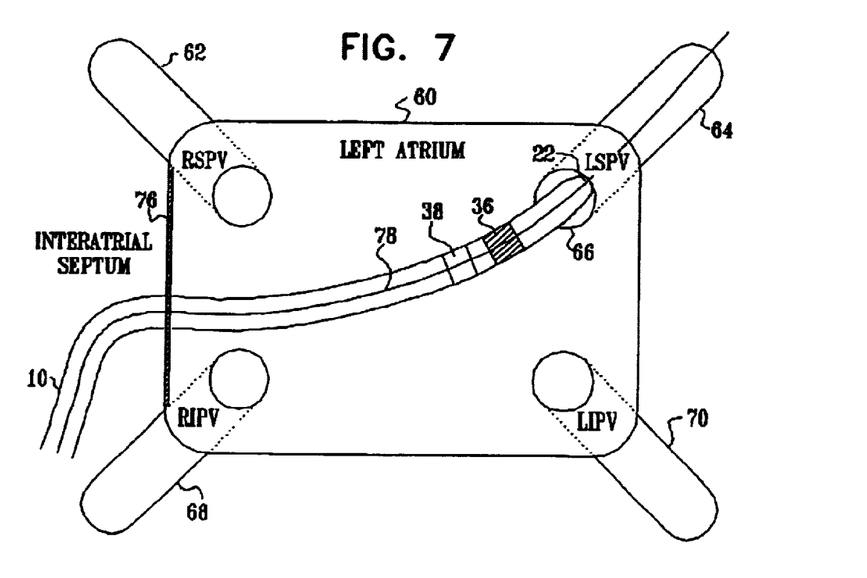
FIG. 7 schematically illustrates certain aspects of a method of intracardiac catheter access during a second phase of the method shown in FIG. 5.

Reference is now made to FIG. 7, which schematically illustrates certain aspects of the method of electrical pulmonary vein isolation in accordance with a preferred embodiment of the invention. The description of FIG. 7 should be read in conjunction with FIGS. 5 and 6. FIG. 7 represents the status at the completion of step 80 (FIG. 5). Structures in FIG. 7 which are identical to corresponding structures in FIG. 6 have been given like reference numerals. The shaft of the catheter 10 extends through the interatrial septum 76. A portion of the anchoring balloon 22 is disposed across the ostium 66 of the left superior pulmonary vein 64. The guidewire 78 is still in position. The optical fiber 28 has not yet been introduced. During placement, the anchoring balloon 22 is deflated.

Referring again to FIG. 5, at step 82 the anchoring balloon 22 is inflated to fix the catheter 10 in position. The guidewire 78 is withdrawn, and the optical fiber 28 is introduced into the catheter 10 via the lumen 24, or is pre-fixed to the distal end of the catheter 10. The mirror 34 is positioned proximal to the anchoring balloon, to be in a position to reflect the laser output of the optical fiber 28, such that the light essentially simultaneously impinges upon an entire ring in or adjacent to the inner lining of the pulmonary vein. Perfusion of the area through one of the catheter ports may be employed during step 82 to minimize stasis of blood in the region.

In step 84, once the position of the mirror 34 is confirmed, the laser light source 32 is energized, and light energy is conducted from the optical fiber 28 to the target tissue.

Figure 8:
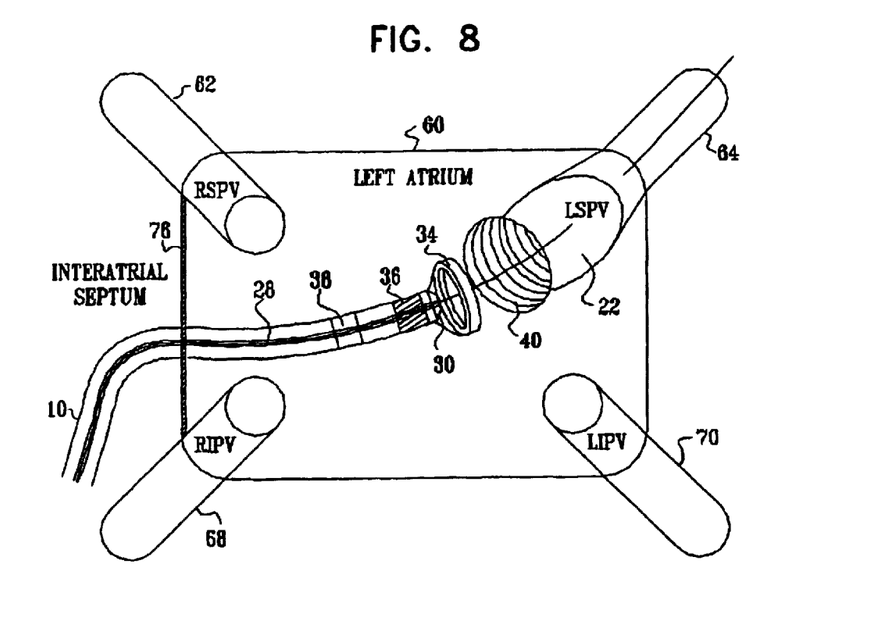
FIG. 8 schematically illustrates certain aspects of a method of intracardiac catheter access during a third phase of the method shown in FIG. 5.

Reference is now made to FIG. 8, which schematically illustrates certain aspects of the method of electrical pulmonary vein isolation in accordance with a preferred embodiment of the invention. The description of FIG. 8 should be read in conjunction with FIGS. 5 and 7, in which like reference numbers denote the same element throughout. FIG. 8 represents the status at step 84 (FIG. 5). The anchoring balloon 22 is inflated, and the optical fiber 28 has been introduced such that its distal end is at the distal end 14 of the catheter 10. The mirror 34 is positioned in readiness for reception of laser light from the optical fiber 28.

Referring again to FIG. 5, the transfer of laser light energy from the optical fiber 28 to the pulmonary vein in step 84 preferably occurs in a single, relatively short application. The output of the laser light source 32 (FIG. 2) is preferably infrared light at about 1.3 microns. This wavelength has a low absorption coefficient in water and is therefore suitable for transfer of energy to the ablation zone. It is recommended to deliver short pulses of energy of a few milliseconds each. Pulses less than 100 milliseconds are most preferred. The energy application may be controlled in response to continuous electrophysiological monitoring, an end point being reached when conduction block is confirmed across the line of ablation. Alternatively, it may continue for a duration predetermined to cause conduction block, substantially without feedback. In this latter case, electrophysiological data recorded while the catheter is still in position are preferably analyzed, so as to determine whether a second period of energy application is desired.

Upon completion of the ablation, in step 86 the anchoring balloon is deflated and the mirror 34 retracted. The tip of the catheter is withdrawn into the left atrial chamber. The optical fiber 28 is also withdrawn from the catheter 10, if appropriate.

Next, at decision step 88, a test is made to determine if more pulmonary veins remain to be electrically isolated. If the determination is affirmative then control proceeds to step 90, where the next pulmonary vein is selected. Control then returns to step 58.

If the determination at decision step 88 is negative, then control proceeds to final step 92. The anchoring balloon is deflated, and the entire apparatus withdrawn from the patient. The procedure thereupon terminates.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art which would occur to persons skilled in the art upon reading the foregoing description.

What is claimed is:

1. An apparatus for electrically isolating a cardiac chamber, comprising:
   a laser;
   an intravascular catheter for introduction into a pulmonary vein proximate an ostium thereof;
   an anchor disposed at a distal end of said catheter for fixation thereof at said pulmonary vein; and
   an optical assembly for conducting laser light energy from said laser in a path extending to a circumferential ablation region within or adjacent an inner lining of said pulmonary vein, said optical assembly being substantially in a non-contacting relationship with said anchor, said path for laser light energy avoiding said anchor;
   wherein said optical assembly comprises: an optical fiber for conducting said laser light energy from said laser; a lens disposed at a distal end of said optical fiber; and a reflector disposed in said path between said lens and said anchor, said reflector being external to an outer surface of said anchor for directing said laser light energy in a circumferential line.

2. The apparatus according to claim 1, wherein said lens comprises a graded index lens.

3. The apparatus according to claim 1, wherein said reflector comprises a parabolic mirror.

4. The apparatus according to claim 1, wherein said reflector comprises a light reflecting external surface of said anchor.

5. The apparatus according to claim 1, wherein said anchor comprises a balloon, adapted to inflate to engage said pulmonary vein.

6. The apparatus according to claim 5, wherein said balloon is bilobate.

7. The apparatus according to claim 5, wherein a proximal portion of said balloon in an inflated state thereof is more expanded than a distal portion of said balloon in an inflated state thereof.

8. The apparatus according to claim 1, wherein said laser light energy is applied to said ablation region in exactly one application.

9. The apparatus according to claim 1, wherein said laser light energy is applied to said ablation region in a series of pulses.

10. The apparatus according to claim 9, wherein a duration of each of said pulses is less than 100 milliseconds.

11. The apparatus according to claim 1, wherein said laser light energy has a wavelength of about 1.3 microns.

12. A method for electrically isolating a cardiac chamber, comprising the steps of:
    introducing an apparatus for electrically isolating a cardiac chamber, comprising:
    an intravascular catheter for introduction into a pulmonary vein proximate an ostium thereof;
    an anchor disposed at a distal end of said catheter for fixation thereof at said pulmonary vein; and
    an optical assembly for conducting laser light energy in a path extending to a circumferential ablation region within or adjacent an inner lining of said pulmonary vein, said optical assembly is substantially in a non-contacting relationship with said anchor, said path for laser light energy avoiding said anchor;
    introducing the optical assembly at said pulmonary vein proximate an ostium of said pulmonary vein;
    anchoring said optical assembly at said pulmonary vein using said anchor; and
    thereafter conducting laser light energy in a path extending from said optical assembly to a circumferential ablation region within or adjacent the inner lining of said pulmonary vein.

13. The method according to claim 12, wherein said step of conducting said laser light energy is performed by directing said laser light energy into a circumferential line that intersects said ablation region.

14. The method according to claim 12, wherein said anchor comprises a balloon, and anchoring is performed by expanding said balloon to engage said pulmonary vein.

15. The method according to claim 12, wherein said step of introducing is performed via a fossa ovalis of a heart, further comprising the step of directing preliminary laser light energy onto said fossa ovalis to ablate tissue thereof to facilitate passage of said optical assembly therethrough.

16. The method according to claim 12, wherein said step of conducting said laser light energy is performed in exactly one application.

17. The method according to claim 12, wherein said step of conducting said laser light energy is performed in a series of pulses.

18. The method according to claim 17, wherein a duration of each of said pulses is less than 100 milliseconds.

19. The method according to claim 12, wherein said step of introducing is performed by disposing said optical assembly on an intravascular catheter; and
    passing a distal portion of said intravascular catheter through a blood vessel into a heart.

20. The method according to claim 12, wherein said step of conducting said laser light energy further comprises reflecting said laser light energy.

21. The method according to claim 20, wherein reflecting said laser light energy comprises disposing a mirror in a path of said laser light energy external to said anchor.

22. The method according to claim 20, wherein reflecting said laser light energy comprises disposing a light-reflective coating on an external surface of said anchor and reflecting said laser light energy from said light-reflective coating.

23. The method according to claim 12, wherein said laser light energy has a wavelength of about 1.3 microns.

* * * * *